United States Patent

Sanford et al.

[11] Patent Number: 5,394,863
[45] Date of Patent: Mar. 7, 1995

[54] VAGINAL FORNIX ILLUMINATOR

[76] Inventors: Theodore H. Sanford, 26 Dana Ave., Lewiston, Me. 04210; Sam Patterson, Unit M, 143 S. Cedros, Solana Beach, Calif. 92075

[21] Appl. No.: 3,393

[22] Filed: Jan. 12, 1993

[51] Int. Cl.⁶ ............................................. A61B 1/30
[52] U.S. Cl. ........................................ 128/3; 128/23; 606/119
[58] Field of Search ............ 128/23, 3, 4, 5–9, 128/13, 18, 22, 20; 606/119, 123, 121, 191

[56] References Cited

U.S. PATENT DOCUMENTS

| | | | |
|---|---|---|---|
| 421,585 | 2/1890 | Kochs et al. | 128/23 |
| 2,055,188 | 9/1936 | Wappler et al. | 128/4 |
| 2,746,450 | 5/1956 | Lady et al. | 128/6 |
| 3,131,690 | 5/1964 | Innis et al. | 128/23 |
| 3,202,152 | 8/1965 | Wood et al. | 606/123 |
| 3,664,330 | 5/1972 | Deutsch | 128/18 |
| 3,685,509 | 8/1972 | Bentall | 606/199 X |
| 3,744,481 | 7/1973 | McDonald | 128/6 |
| 3,771,516 | 11/1973 | Corriero | 128/23 |
| 3,774,614 | 11/1973 | Cook | 128/23 X |
| 3,945,371 | 3/1976 | Adelman | 128/6 X |
| 3,948,270 | 4/1976 | Hasson | 606/199 X |
| 4,337,763 | 7/1982 | Petrassevich | 128/20 |
| 4,430,076 | 2/1984 | Harris | 606/119 X |
| 4,449,519 | 5/1984 | Sarrine | 128/4 |
| 4,562,832 | 1/1986 | Wilder et al. | 128/20 |
| 4,597,383 | 7/1986 | Van Der Bel | 128/18 |
| 4,683,879 | 8/1987 | Williams | 128/6 X |
| 4,836,186 | 6/1989 | Scholz | 128/20 X |
| 4,901,708 | 2/1990 | Lee | 128/11 |
| 5,019,086 | 5/1991 | Neward | 606/123 |
| 5,131,380 | 7/1992 | Heller et al. | 128/6 |
| 5,143,054 | 9/1992 | Adair | 128/18 |
| 5,209,754 | 5/1993 | Ahluwalia | 128/20 X |

FOREIGN PATENT DOCUMENTS 215409 4/1968 U.S.S.R. .................. 606/123

OTHER PUBLICATIONS

"Acrylic Resins," D. S. Frederick, *Modern Plastics*, pp. 32 and 108.

*Primary Examiner*—Richard J. Apley
*Assistant Examiner*—Donna L. Maraglio
*Attorney, Agent, or Firm*—Aquilino & Welsh

[57] ABSTRACT

A pipe like optical wave guide illuminator transmits light from a fiber optic source through a light transmissive plastic body. The body has an elongated stem and a cup, with a hollow in the cup. The cup is engagable over the cervix and light is transmitted through the rim of the cup through the vaginal fornix in aid of surgical and medical procedures.

7 Claims, 3 Drawing Sheets

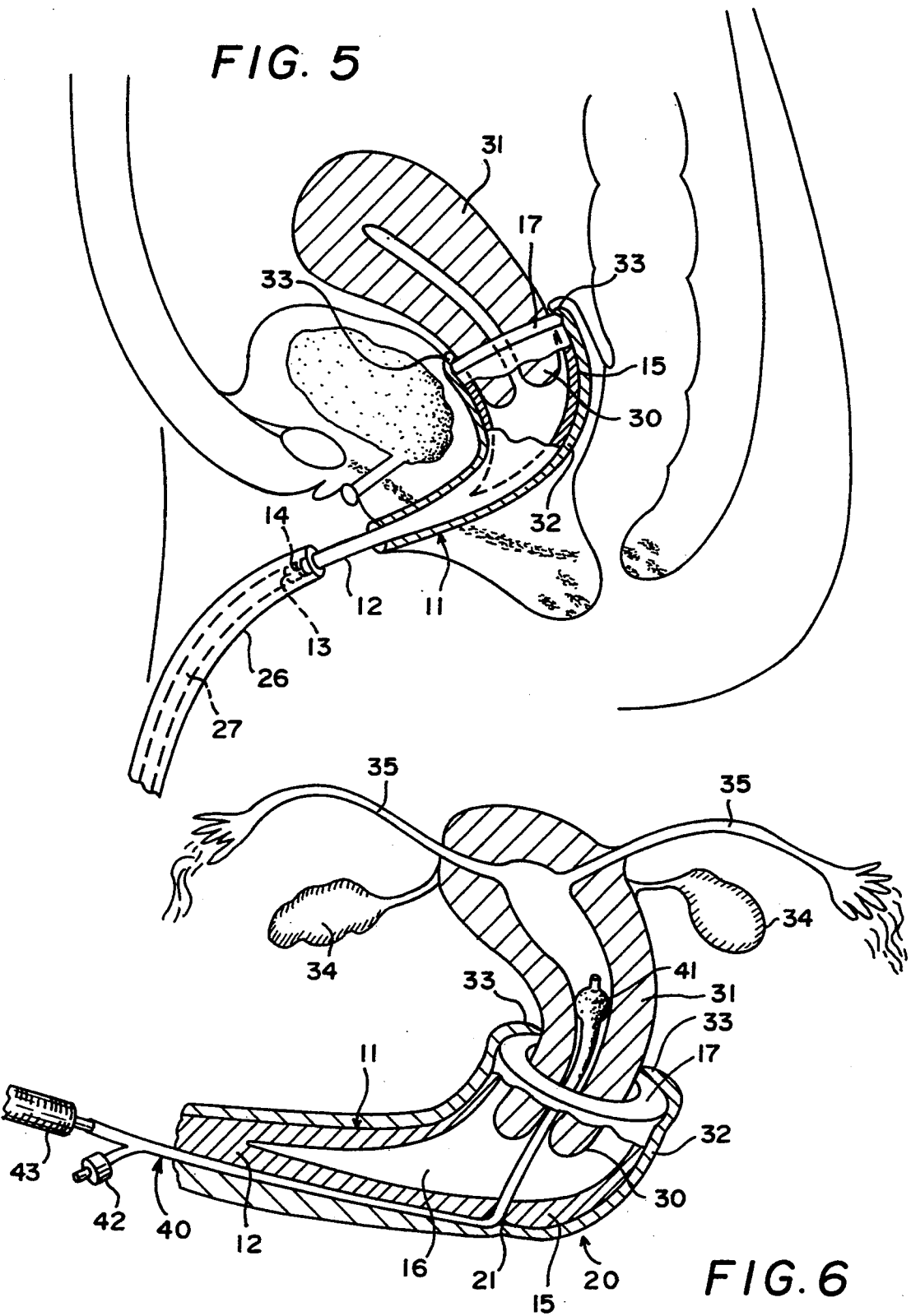

VAGINAL FORNIX ILLUMINATOR

BACKGROUND OF THE INVENTION

The present invention is a vaginal fornix trans illuminator. It is a clear, molded light transmitting plastic instrument, preferably of LUCITE ®, or an appropriate light transmitting acrylic resin. The instrument illuminates thin tissues and transmits light through the tissues so that easy identification of the fornix particularly from above, as seen through a body cavity is possible for medical procedures, to examine, to use in surgery or in theraputic procedures.

Heretofore, the fornix could not be easily identified scientifically from above, only by guess work or feel. In surgical procedures, this oftentimes resulted in the removal of excess vaginal tissue, such as during an abdominal hysterectomy.

The trans illuminator illuminates the fornix and demonstrates to a surgeon exactly where the tissues are to be cut to remove the cervix from its surrounding attachments during an abdominal hysterectomy. Because of the tension of the vaginal tissues, blood loss is decreased and easy side to side approximation of the vaginal tissues is carried out over the edges of the lighted trans illuminator.

In the past, blood from the cutting of the vaginal tissues surrounding the cervix would flow into the vagina. The usual practice was to aspirate this blood gathered in the vagina, thus contaminating intra abdominal tissues with blood from the contaminated area of the vagina. With the trans illuminator in place, blood escapes into the "cup" of the trans illuminator and is easily aspirated.

Using the present invention during pelviscopy, it is possible to determine exactly where the vagina is. Heretofore, a cotton gauze sponge was placed in the vagina to identify that anatomical area. When using a YAG or $CO_2$ laser, there was always a possibility of ignition of the gauze in the vagina. Using the trans illuminator of the present invention the exact location of the vaginal fornix is identified by the firmness of trans illuminator and the light.

The present invention is useful in the treatment of endometriosis via laparoscopy or the performance of a hysterectomy via pelviscopy, using a laparoscopically video directed procedure from above and in the treatment of infertility and pelvic inflamminatory disease, or any tubal occluding process.

Hydrotubation of the uterus may be carried out at the same time the trans illuminator is applied to the vagina. Hydrotuberation is carried out by placing a foley catheter into the cup portion end of the illuminator, passing it directly into the uterus and filling the foley balloon with water or air. The trans illuminator is directed along the catheter and surrounds the cervix filling the vaginal fornix. Hydrotubation is carried out by passing Indigo Carmin into the uterus via the catheter and the dye (Indigo Carmin) is visualized, spilling from the tubal lumen, demonstrating tubal patency, or no dye appearing which demonstrates tubal occlusion, all under direct vision of the laparoscopically directed video camera. This is part of an infertility workup. If infertility is a problem, the illuminated fornix would identify clearly the vagina, especially if laser procedures were to be performed.

Uterine manipulation upward or to the sides can be carried out with the trans illuminator in place. Because the cervix is placed in the trans illuminator in close approximation to the sides, the uterus can be positioned as desired in the pelvis, in order to facilitate surgical procedures from the above, through the laparoscope. The lighted edges of the instrument gives the operator clear definition of the vaginal fornix.

DESCRIPTION OF THE RELATED ART

U.S. Pat. No. 4,449,519 discloses an endoscope tube, which merely includes a press fit fiber optic light.

U.S. Pat. No. 5,143,054 discloses a cervical videoscope with detachable camera unit. The video camera unit is removably attached to one blade of the speculum, as by a flexible strap. The videoscope is illuminated by a surrounding band of optical fibers attached to a light source. Light emanates directly from the fiber to the subject.

U.S. Pat. No. 5,131,380 discloses a softwall medical tube with a fiber optic light conductor. The device involves the combination of a transparent medical tube and a flexible light conductor which is slidably and removably disposed therein. Light transmitted by the conductor to its distal end passes outwardly through the medical tube's distal end wall, and may be visually and externally observed through the body wall of the patient, to identify the approximate position of a tube within the body.

U.S. Pat. No. 4,337,763 discloses an illuminated surgical instrument. The instrument is a speculum or retractor with a projecting light fixture with an incandescent battery operated light which points into the body cavity.

U.S. Pat. No. 4,597,383 discloses a fiber optic illuminated vaginal speculum. The invention includes a fiber optic light attachment for a vaginal speculum which is adapted to be mounted on the base portion of a conventional speculum and which is adapted for projecting a beam of light within the viewing channel from the end of the fiber optic bundle which is held between the jaws of the speculum.

U.S. Pat. No. 4,562,832 discloses a medical instrument and light pipe illumination assembly fabricated of synthetic plastic material. The invention involves a medical instrument associated with a flexible light guide in a monofilament core pipe format with a cladding tube to deliver light to a desired site. The same pipe can be used as a glow tube when provided with a disbursant in the plastic of an optical fiber. In a preferred embodiment of the light pipe, the core is a monofilament of resinous material having a relatively high refractive index capable of transmitting light by internal reflection.

U.S. Pat. No. 3,945,371 discloses an apparatus for inspection and sampling in restricted aperture cavities employing fiber optics. The apparatus has a body portion carrying a probe, the housing, the image display means and optical means. Two fiber optic bundles are used one for carrying light to the point to be observed and another to catch the image which is brought to a ground glass display panel.

U.S. Pat. No. 4,901,708 discloses a viewing laryngoscope. The laryngoscope enables one performing a laryngoscopy to have a clear view of the area adjacent to the distal tip of a curved type laryngoscope blade member while inserting the blade member into the throat of a patient. To achieve this, fiber optic bundles are incorporated along a blade member, one fiber optic bundle transmitting light from a light source located near the proximal end of the blade member to a point along the distal end of the blade member and another fiber optic bundle being coupled to a lens located at the proximal end of the blade member to provide telescopic viewing of the area adjacent to the distal end of the blade member.

U.S. Pat. No. 3,664,330 discloses a fiber optic medical tool and also provided for is fiber optic lighting. The invention provides manipulative access, illumination and visualization within a body orifice, and it includes a device which has a pair of substantially parallel elongated members having distal ends adapted to extend into the body orifice to provide manipulative access to the body area interior of the orifice.

U.S. Pat. No. 3,744,481 discloses a medical examining method and means. The invention allows viewing the cervix and vaginal segment of a human uterus including light transmitted by fiber optic principles through the blades to illuminate. It is comprised of two, three or four elongated blades which are removably mounted on a holder. The blades are adjustable to spread and to retain the vaginal walls including the cervico-vaginal fornix for visual observation and accessibility of surgical instruments to the uterus.

SUMMARY OF THE INVENTION

The prior art describes many different fiber optic light medical instruments, employing illumination and fiber optic illumination. However, the prior art does not show nor suggest the structural configuration or use of light directed about the cervix, through the fornix, for the trans illumination of the fornix.

The present invention includes a fiber optic light source such as a plastic tube with a bundle of fiber optic fibers to snap over the end of the device, engaging the fiber optics adjacent to the end of the trans illuminator. The trans illuminator is made of LUCITE ® and transmits the light from the end of the pipe like device to the round cup that is engaged about the cervix at its fornix.

The device trans illuminates the fornix of the vagina, so that medical procedures can be carried on, particularly from above, with the vaginal fornix outlined in light through the trans illuminator below.

The trans illuminator is shaped to the anatomical configuration and dimensions of the vagina. A fiber optic cord is attached to the end of the instrument, which brightly illuminates its edges, giving it the ability to penetrate vaginal tissues with a cool light. The light source produces the brightest light available to instrumentation and the clear LUCITE ® of the instrument transmits light most efficiently. Near the end of the instrument, in one version, is a hole through which a foley catheter can be passed, making the trans illuminator adaptable to intubation.

The instrument can be used to illuminate vaginal fornix as well as manipulate the uterus. Aspiration of blood from the trans illuminator cup eliminates contamination of the pelvic and abdominal tissues.

Hydrotubation can be carried out while the instrument is being used for anatomical identification and manipulation.

According to the present invent ion an optical wave guide trans illuminator for the vaginal fornix has a light transmissive plastic body shaped like a pipe. The pipe has an elongated stem and a cup. The stem has an end and the cup forms a hollow opening in the body extending from the stem and through the cup opening. The cup engages the cervix. A fiber optic light source is attachable to the stem.

The body may be an acrylic resin. The hollow may taper outward from within said stem includes the cup. The hollow may terminate within the stem and the opening may define a rim from which light may be transmitted from the fiber optic light source through the rim and through the fornix.

The end of the stem may be flat. The may stem include an inset where the fiber optic light source may be attached.

The may be a further opening through the body into the hollow which may be pluggable.

A vaginal manipulator or a catheter may be engaged and used through the further opening.

Although such novel feature or features believed to be characteristic of the invention are pointed out in the claims, the invention and the manner in which it may be carried, may be further understood by reference to the description following and the accompanying drawing.

BRIEF DESCRIPTION OF THE DRAWINGS

FIG. 5 is a side elevation sectional view through a woman's body, of the trans illuminator of FIG. 1 in place with an attached fiber optic light source.

FIG. 6 is a detail cut away side elevation of the trans illuminator of FIG. 4 in the vagina with a foley catheter engaged therethrough in the uterus.

Referring now to the figures in greater detail, where like reference number denote like parts in the various figures.

DESCRIPTION OF THE PREFERRED EMBODIMENTS

Figure 1:
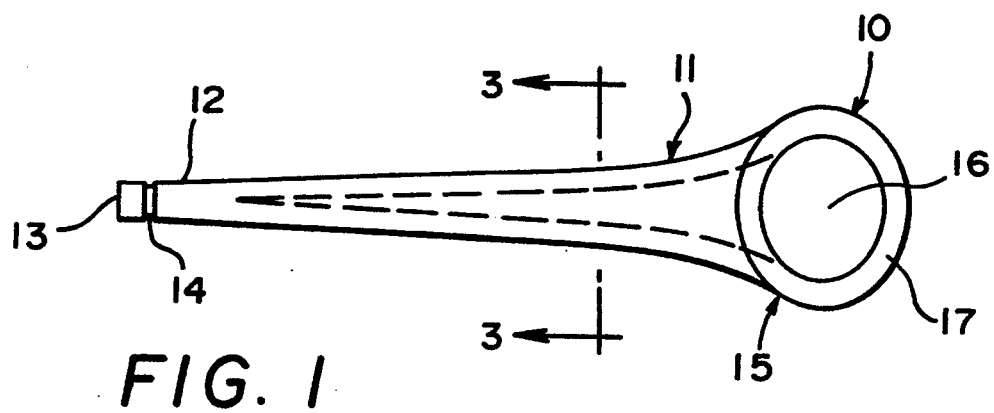
FIG. 1 is a plan view of the trans illuminator of the present invention.
Figure 2:
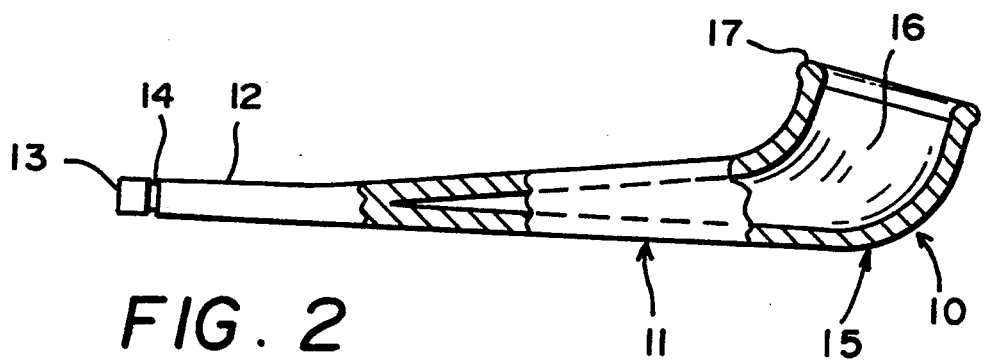
FIG. 2 is a cut away side elevation of FIG. 1.
Figure 3:
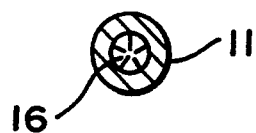
FIG. 3 is a section of FIG. 1 at lines 3—3.

As shown in FIGS. 1–3 the trans illuminator 10 has a pipe like body 11 witch a stem 12 and at one end an end 13. There is an inset 14 on stem 12. At the other end of the body 11 is a cup 15 which opens into a hollow 16 which extends part way into the stem 12 which is tapered. The cup 15 has a peripheral rim 17.

Figure 4:
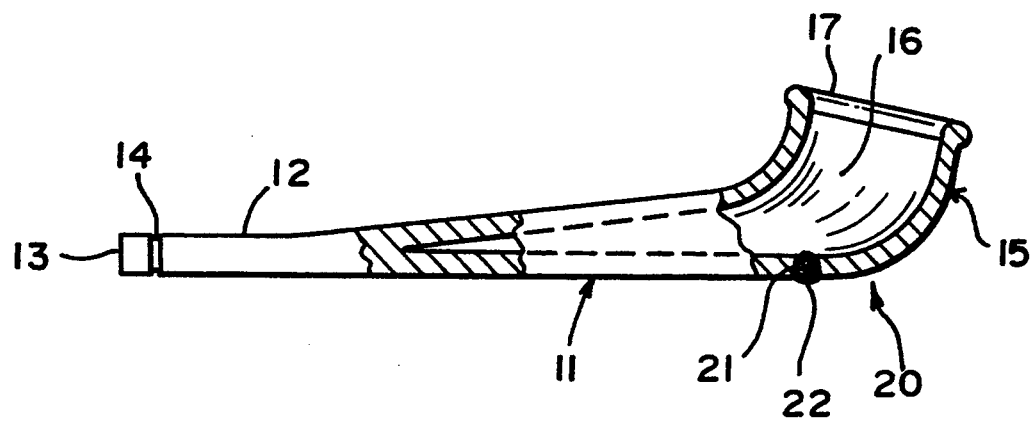
FIG. 4 is a cut away side elevation of the trans illuminator of the present invention, with a plugged opening.

As shown in FIG. 4, the trans illuminator 20 includes an opening 21, which can be plugged with a plug 22.

IN USE

As shown in FIG. 5, the stem 12 of the body 11 is connected to a tube 26 which contains a fiber optic bundle 27 leading to a remote light source (not shown). The tube 26 engages the stem 12 at the inset 14, holding it to fiber optic bundle 27 at the end 13, so that light can be transmitted through the body 11.

As shown in FIG. 5, the body 11 is in the vagina 32 with the cervix 30 of the uterus 31 engaged in the cup 15. The rim 17 of the cup 15 is at the fornix 33 of the vagina 32. Light from the fiber optic bundle 27 passes through the body 11 from the end 13 of the stem 12 and exits from the rim 17 of the cup 15 trans illuminating the fornix 33. The fornix 33 is thus visible and defined inside the body cavity for the purpose of executing surgical or medical procedures.

The trans illuminator 10 illuminates the fornix 33 and demonstrates to a surgeon exactly where the tissues are to be cut to remove the cervix 30 from its surrounding attachments during an abdominal hysterectomy. Blood loss is decreased and easy side to side approximation of the tissues of the vagina 32 is carried out over the rim 17 of the lighted trans illuminator 20.

As shown in FIG. 6, the body 11 of the trans illuminator 20 is in the vagina 32 with the cervix 30 of the uterus 31 engaged in the cup 15. The rim 17 of the cup 15 is at the fornix 33 of the vagina 32. The light, as shown in FIG. 5 from the fiber optic bundle 27, passes through the body 11 from the end 13 of the stem 12 and exits from the rim 17 of the cup 15 trans illuminating the fornix 33. The fornix 33, each ovary 34 and each fallopian tube 35 is thus visible from inside the body cavity from above for the purpose of executing surgical or medical procedures.

Hydrotubation of the uterus 31 may be carried out by removing the plug 22, placing a foley catheter 40 through the opening 21 in the body 11 and through the cup 15 of the trans illuminator 20, passing it directly into the uterus 31 and filling the foley balloon 41 with water or air and then closing the valve 42. Hydrotubation is carried out by using a syringe 43 and passing Indigo Carmin into the uterus 31 via the foley catheter 40. A dye can be seen from above, spilling from the fallopian tubes 35, demonstrating tubal patency, or no dye appearing which demonstrates tubal occlusion, seen through a laparoscopically directed video camera (not shown). This is part of an infertility workup. If infertility is a problem, the illuminated fornix 33 would identify clearly the vagina 32, especially if laser procedures were to be performed.

Figure 7:
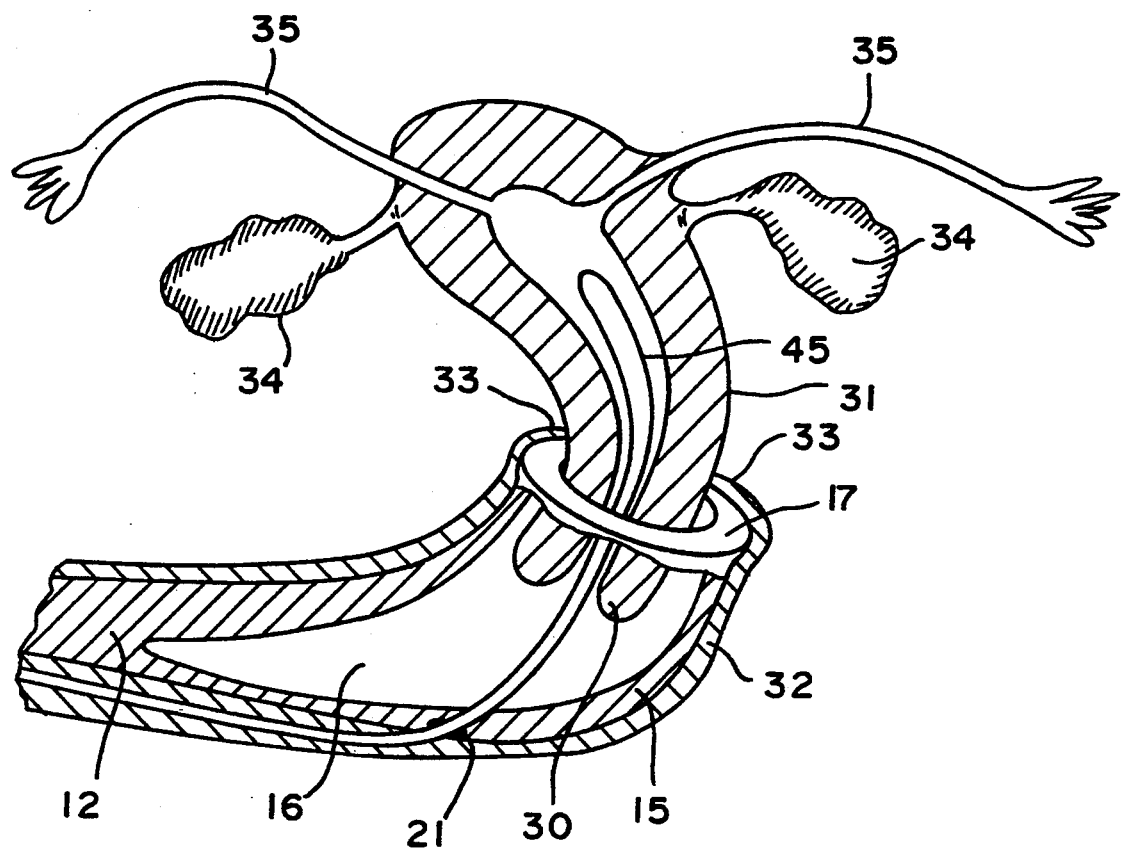
FIG. 7 is a detail cut away side elevation of the trans illuminator of FIG. 4 in the vagina, with an uterine manipulator.

Uterine manipulation upward or to the sides can be carried out with the trans illuminators 10. 20, in place for procedures, and as shown in FIG. 7, manipulation of the uterus 31 may be carried out by removing the plug 22, placing a uterine manipulator 45 through the opening 21 in the body 11 and through the cup 15 of the trans-illuminator 20, passing it directly into the uterus 31. Manipulation may be carried out directly or in conjunction with manipulation of the trans-illuminator 20.

Blood from the cutting of the vaginal tissues surrounding the cervix 30 may now flow into the hollow 16 of the cup 15 of the trans illuminator 10 or into the trans illuminator 20 with the plug 22 engaged then easily aspirated from above.

The terms and expressions which are employed are used as terms of description; it is recognized, though, that various modifications are possible.

It is also understood the following claims are intended to cover all of the generic and specific features of the invention herein described, and all statements of the scope of the invention which, as a matter of language, might fall therebetween.

Having described certain forms of the invention in some detail, what is claimed is:

1. An illuminating instrument for the vaginal fornix comprising a substantially pipe-shaped light transmissive plastic body having a cup, a hollow, and an elongated stem with a longitudinal axis, said stem having a free end with means to attach a light source thereto, said cup having an opening and extending outwardly from said stem in a direction generally perpendicular to the longitudinal axis of said stem, said opening having a rim sized to engage a cervix, said hollow extending from said opening into said stem toward said free end and terminating before said free end of said stem.

2. The invention of claim 1, wherein the stem tapers outwardly from said free end into said cup.

3. The invention of claim 1, further including a light source attached to said stem which transmits light through said stem and out through the rim of said cup.

4. The invention of claim 3, wherein said light source is in the form of a fiber optic bundle.

5. The invention of claim 1, wherein said cup includes an aperture separate from said opening in said cup.

6. The invention of claim 5, wherein said aperture is closed by a plug.

7. The invention of claim 5, in combination with a means to manipulate a uterus insertable through said aperture.

* * * * *